(12) United States Patent
Dillon

(10) Patent No.: US 7,087,135 B2
(45) Date of Patent: Aug. 8, 2006

(54) PROCESS FOR THE MANUFACTURE OF INTERPENETRATING POLYMER NETWORK SHEETING AND USEFUL ARTICLES THEREOF

(75) Inventor: Mark E. Dillon, Allentown, PA (US)

(73) Assignee: Bio Med Sciences, Inc., Allentown, PA (US)

( * ) Notice: Subject to any disclaimer, the term of this patent is extended or adjusted under 35 U.S.C. 154(b) by 65 days.

(21) Appl. No.: 10/714,439

(22) Filed: Nov. 14, 2003

(65) Prior Publication Data

US 2005/0106327 A1     May 19, 2005

(51) Int. Cl.
*B29C 65/00*     (2006.01)

(52) U.S. Cl. .................. 156/285; 156/329; 427/2.1; 427/2.31; 427/208.2; 427/387; 428/40.1; 428/41.4; 428/304.4; 428/306.6; 428/308.4; 428/313.5; 428/315.5; 428/317.1; 428/317.7; 428/318.4; 428/320.2; 428/321.1; 428/421

(58) Field of Classification Search ............ 428/315.9, 428/447; 427/387, 294, 296, 350; 156/329
See application file for complete search history.

(56) References Cited

U.S. PATENT DOCUMENTS

| 4,832,009 A | * | 5/1989 | Dillon ..................... 602/58 |
| 5,009,224 A | * | 4/1991 | Cole ....................... 602/52 |
| 5,702,503 A | * | 12/1997 | Tse Tang ................. 95/45 |
| 5,919,330 A | * | 7/1999 | Pall et al. ............... 156/305 |
| 6,235,662 B1 | * | 5/2001 | Zehnder ................. 442/223 |

FOREIGN PATENT DOCUMENTS

| GB | 2155851 A | * | 10/1985 |
| JP | 61-40328 A | * | 2/1986 |

* cited by examiner

*Primary Examiner*—Marc S. Zimmer
(74) *Attorney, Agent, or Firm*—John F. A. Earley; John F. A. Earley, III; Harding, Earley, Follmer & Frailey

(57) ABSTRACT

A novel method of producing interpenetrating polymer network ("IPN") sheeting. Particularly, an improved method of producing such sheeting and bonding it to a backing layer for use as various types of wound dressings and scar management products. The new process represents several improvements over previous techniques as follows: a) single-pass process, b) no second coating of liquid polymer required to act as glue, c) no solvents or other processing aids required, d) no additional oven length needed to effect the required dwell time, e) increased line speed relative to prior techniques, and g) the carrier substrate 20 need only be coated with a release surface on one side.

22 Claims, 3 Drawing Sheets

PROCESS FOR THE MANUFACTURE OF INTERPENETRATING POLYMER NETWORK SHEETING AND USEFUL ARTICLES THEREOF

BACKGROUND OF THE INVENTION

1. Field of the Invention

This invention relates to a novel method of producing interpenetrating polymer network ("IPN") sheeting. Particularly, this invention relates to an improved method of producing such sheeting for use as various types of wound dressings and scar management products.

2. Description of the Prior Art

U.S. Pat. No. 4,832,009 issued May 23, 1989 to Mark E. Dillon and assigned to Bio Med Sciences, Inc., and U.S. Pat. No. 5,980,923, issued Nov. 9, 1999 to Mark E. Dillon, also assigned to Bio Med Sciences, Inc., Allentown, Pa., the disclosures of which are incorporated herein by reference, describe wound dressings and scar management materials comprised of IPN sheets and in particular IPN sheets of polydimethylsiloxane ("PDMS") and polytetrafluorethylene ("PTFE"). Interpenetrating polymer networks are defined as a blend of two or more polymers where each material forms a continuous network, each network interpenetrating the other (Sperling, Interpenetrating Polymer Networks and Related Materials Plexem Press, New York, 1981). An IPN is therefore a type of polymer/polymer composite. In each of the above referenced patents a process is used for creating PTFE/PDMS IPN sheeting in which a liquid PDMS composition is impregnated into a microporous or expanded PTFE ("ePTFE") membrane. This process involves casting the liquid PDMS onto the ePTFE membrane or alternatively casting the liquid PDMS onto a carrier substrate and laying-down the ePFTE membrane onto the Liquid PDMS layer. In either case natural wicking occurs by way of capillary action to effect impregnation of the PDMS liquid layer into the ePTFE membrane. The resultant IPN sheet is then exposed to heat or some other method of vulcanization causing the liquid PDMS to crosslink into a solid elastomer or gel thereby creating the IPN sheet.

This technique may be employed using a static system for single sheets of IPN or a continuous system to produce rolls of IPN of almost any desired length. For thermally crosslink PDMS formulations an oven is typically used to effect crosslinking of the PDMS. In the static system approach a closed convection oven may be employed. For the continuous method the IPN sheets may be passed through a tunnel style oven and wound into a roll.

The above methods are used by the Applicant to produce a variety of IPN sheets. For example, for the production of wound dressing sheets, a thin (0.002 in. or 50 microns) PTFE/PDMS IPN sheet is produced in continuous rolls and then coated with an additional layer of PDMS to provide an adhesive surface to one side of the IPN sheet. This is accomplished by passing the IPN sheet through the system twice; first to create the IPN sheet and second to impart increased adhesiveness by adding a layer of additional PDMS to the skin-contacting side of the IPN sheet.

Another example is for the production of scar management sheets. In this case, a relatively thick layer 10 (0.025 in. or 635 microns) of liquid PDMS is cast onto a carrier substrate 20 (FIG. 4) and the ePTFE membrane 30 is laid on top of the liquid PDMS layer 10 and the impregnation process is effected by capillary wicking. This technique provides a sheet 12 comprising a layer of IPN and a layer of pure PDMS, this creating one side of the sheet that is more adhesive than the other while using a single-pass process. This is due to the extent to which the wicking process occurs. The small pores within the ePTFE membrane 30 act as capillaries and essentially pull the liquid PDMS into the void spaces of the membrane 30 due to the surface tension force between the capillary walls and the liquid PDMS. For thin membranes 30 with small pore sizes this force is enough to bring the liquid to the distal or upper surface 25 of the membrane 30 at which point the surface tension force within the capillaries is relieved and the wicking process stops. The resultant sheeting material is essentially 100 percent PDMS on the skin-contacting surface 15 while the distal or upper surface 25 is comprised of the IPN polymer blend structure.

While the difference between adhesiveness levels of the two surfaces 15 and 25 can be significant, there are cases where even greater disparity is desired. For example, the Applicant produces a scar management product (marketed as Oleeva® Fabric; OLEEVA®is the trademark of Bio Med Sciences, Inc., Registration No. 2,446,261, registered Apr. 24, 2001, for topical sheeting for the prevention and management of dermal scars) where the distal or upper surface 25 of the IPN sheet 12 is bonded to a textile fabric 40 so that garments worn over the product slide easily over the textile fabric 40 and any tendency for the sheet 12 to roll-up or cling to such garments is reduced or eliminated. This design is accomplished by using a two-pass process whereby the IPN sheet of the previous example is coated on the IPN upper surface 25 with an additional layer 50 of liquid PDMS onto which the textile fabric 40 is laid. The additional layer 50 (FIG. 1) of liquid PDMS serves as glue and bonds the fabric 40 to the IPN upper surface 25. While a two-pass process is undesirable for obvious reasons (including economic factors such as processing time and handling expenses as well as quality aspects such as increased defects), numerous attempts at reducing the Oleeva® Fabric process to a single pass have been unsuccessful.

For continuous methods one obvious approach to reducing the process to a single pass would to be to install a second coating station between two sections of the tunnel oven and apply the second layer 50 of PDMS and the textile fabric 40 in-line. This approach was not an option to the Applicant due to the additional floor space required to install a second tunnel oven. Simply cutting the existing oven in half and installing a second coating station in the middle would not have been a desirable approach because this would effectively cut the line speed of the process in half. The crosslinking reaction of the PDMS is dependent on dwell time in the oven. A shorter oven means a slower line speed to maintain the same dwell time. Since the first layer 12 of IPN sheet must be sufficiently cured before it contacts any machine parts or rollers (or it will have a tendency to stick and/or cause the PDMS to migrate) the line speed would have to be reduced by half to provide a material capable of being passed through the rollers required for the second coating process. This approach would therefore essentially double the time required to process the material and require a significant capital investment in a second coating station.

SUMMARY OF THE INVENTION

I have unexpectedly discovered that the production of products such as Oleeva® Fabric can be accomplished using a single-pass technique instead of the conventional two-pass process. To accomplish the process of this invention, the ePTFE membrane 30 is applied to the surface of the liquid PDMS layer 10 as previously described; however, with the new process the IPN sheet 12 is not vulcanized until after the textile fabric 40 has also been applied. With initial trials this technique provided unsatisfactory results in that no significant bond was achieved between the IPN upper surface 25 and the fabric 40. It is believed that this was due to the natural tendency for the wicking process to stop at the upper surface 25 of the ePTFE membrane 30 and therefore not achieve sufficient bond to the fabric 40.

The application of pressure in an attempt to assist the flow of liquid PDMS to the upper surface 25 of the ePTFE membrane 30 in sufficient quantity to effect a bond to the fabric 40 was problematic for a number of reasons. The applied pressure caused the underlying liquid silicone to migrate away from the pressure point reducing the overall thickness of the end product. Additionally this caused an unstable build-up of material upstream of the pressure point. Even with these problems a sufficient bond between the IPN surface 25 and the fabric 40 was not achieved.

The shortcomings in the pressure application process were partially overcome with the use of solvents as a processing aid. By mixing trichloroethane into the liquid PDMS its viscosity was sufficiently lowered so that a minor level of adhesion between the IPN sheet 12 and fabric 40 was achieved either by more complete wicking or perhaps by "pull through" as the solvent volatilized. This technique, however, did not provide a bond that was capable of withstanding any significant level of peeling stress as evidenced by a tendency of the fabric 40 to delaminate from the IPN sheet 12 when attempting to remove the final product, the composite dressing 52, from the carrier substrate 20. This technique also introduces the additional expense of using such a processing aid and causes an undesirable ecological condition of having to volatilize the solvent.

A satisfactory method of achieving a high quality bond between the fabric 40 and the IPN sheet 12 to form fabric composite sheet 52 without requiring a second pass through the process or the use of solvent was achieved by applying a slight amount of continuous pressure to the surface of the fabric composite sheet 52 as it passed through the tunnel oven 60 during the curing process. This was achieved by following a serpentine path through the oven, i.e. over one idler roll, under the next, over the next, etc. and by placing "S" curves 70, FIGS. 5 and 6, in the web path at one or more points in the oven. This technique applied a slight amount of pressure to the surface of the fabric composite sheet 52 throughout the process and resulted in an effective bond between the IPN sheet 12 and the textile fabric 40 without causing the liquid PDMS to migrate.

It was further found that the application of vacuum to the surface of the fabric 40 further improved the effectiveness of the new process. The vacuum was applied using a vacuum roller to the upper surface 35 of the textile fabric 40 prior to entry into the oven 60 (FIG. 6) to follow the serpentine and "S" curve path 70. It is believed that the application of vacuum in this fashion caused enough of the liquid PDMS 10a (FIG. 2) to migrate past the upper surface 25 of the IPN sheet 12 and into the bottom surface 45 of the fabric 40 as to provide a high quality bond 67 between the layers 40 and 10a.

An additional method of this invention is to utilize an ePTFE membrane which has previously been laminated to the backing material. This method eliminates the sensitivity of an effective impregnation on achieving a high quality bond between the backing material and the IPN. For example, ePTFE film can be laminated to textile fabrics using well-established processes of hot melt adhesive bonding or thermobonding. With the hot melt technique a dot-pattern of molten adhesive is applied to either the ePTFE or the backing material and the two are brought into contact usually under pressure using a nip roller apparatus of the like. For thermobonding the two components are heated sufficiently that one material at least partially melts and a bond is then achieved by applying pressure to the materials using a nip roller apparatus or the like. Either technique may be used with the process of this invention.

The new process represents several improvements over previous techniques as follows:

1) Single-pass process
2) No second layer 50 of PDMS required to act as glue
3) No solvents or other processing aids required
4) No additional oven length needed to effect the required dwell time
5) Increased line speed since the PDMS layer 10 need not be fully crosslinked by the end of the process. The upper surface 35 of the fabric layer 40 contacts any down-line machine parts and rollers so there is no tendency for the material to stick to rollers and the like.
6) The carrier substrate 20 need be coated with a release surface on only one side. The prior technique required a base paper carrier substrate coated with a polymer resin on both sides since the upper surface 25 of the IPN sheet 12 ultimately contacted the backside of the paper carrier substrate 20 when it was rewound into a roll during the first pass. The second release coating was required to avoid unintentional adhesion of the IPN sheet to the backside of the carrier substrate 20. The presence of the fabric 40 during the first pass eliminates this tendency.

DETAILED DESCRIPTION OF PREFERRED EMBODIMENTS

Figure 1:
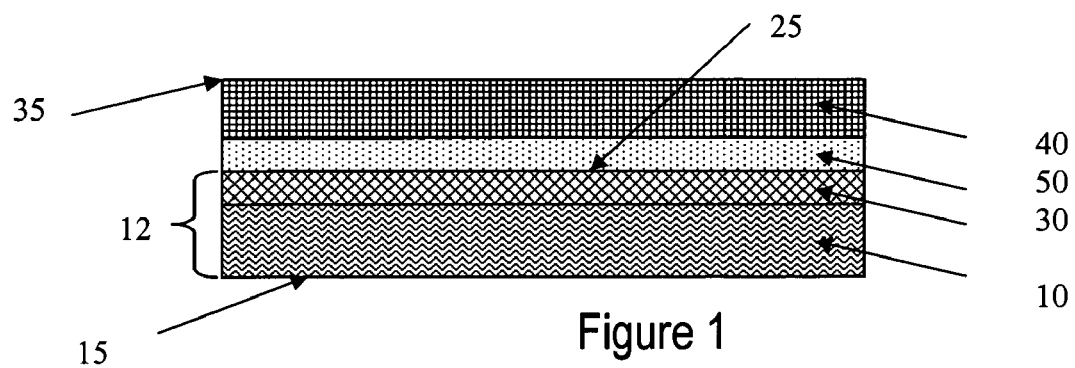
FIG. 1 is a cross-sectional view of the prior art material where a PDMS layer 10 is impregnated into an expanded PTFE membrane 30, which is bonded to textile fabric 40 by means of an additional PDMS glue layer 50 at its distal or upper surface 25.

The following examples of the invention are not intended to be limiting, as changes of these designs and processes could be made without departing from the broad inventive concept of the invention. Likewise, it is believed that some materials could be substitute in this process to achieve products useful for a variety of applications beyond wound care and scar management. In particular, materials other than textile fabrics, such as nonwoven films, foams and the like, could be used.

EXAMPLE 1

A 15 inch (38 cm) wide roll 80 of polymer coated carrier substrate 20 was unwound at a speed of approximately 1 foot (30 cm) per minute. The carrier substrate 20 was then passed through a knife-over-roll coating station with a reservoir 9 of liquid PDMS 10 arranged as to deposit a coating 11 of liquid PDMS onto an 11.5 inch (29 cm) wide section of the carrier substrate 20. The gap between the surface of the carrier substrate 20 and the knife 90 was set at 0.020 inches (500 microns). A 0.0003 inches (8 microns) thick and 12 inch (30 cm) wide roll 31 of ePTFE membrane 30 was unwound onto the surface of the liquid PDMS coating 11. A 14 inch (36 cm) wide roll 41 of tricot textile fabric 40 was then unwound onto the surface of the ePTFE membrane 30.

The unwind apparatus for the ePTFE membrane 30 was set at approximately 6 inches (15 cm) down line from the knife assembly 90 and the fabric unwind 41 was set at approximately 8 inches (20 cm) down-line from the ePTFE unwind 31. In each case the unwind apparatus was arranged so that the roll goods were wrapped around an idler roll 33, 43 positioned slightly above the substrate 20. The next down-line support idler 46 was positioned relative to idler 43 to effect a slight angle so that the substrate 20 with its liquid PDMS coating 11 was gently brought into contact with the ePTFE membrane 30 and fabric 40.

The material was then passed through a 12 foot (3.7 meter) long tunnel style oven 60 utilizing the serpentine and "S" curve design 70. The air temperature within the oven 60 was approximately 180 degrees Fahrenheit (82 degrees Celsius). As the material exited the end of the tunnel oven 60 it was wound into a roll using a tension controlled take-up apparatus (not shown). The roll stock was then fed through a rotary die-cutting apparatus to cut individual pieces for end-use.

EXAMPLE 2

Figure 6:
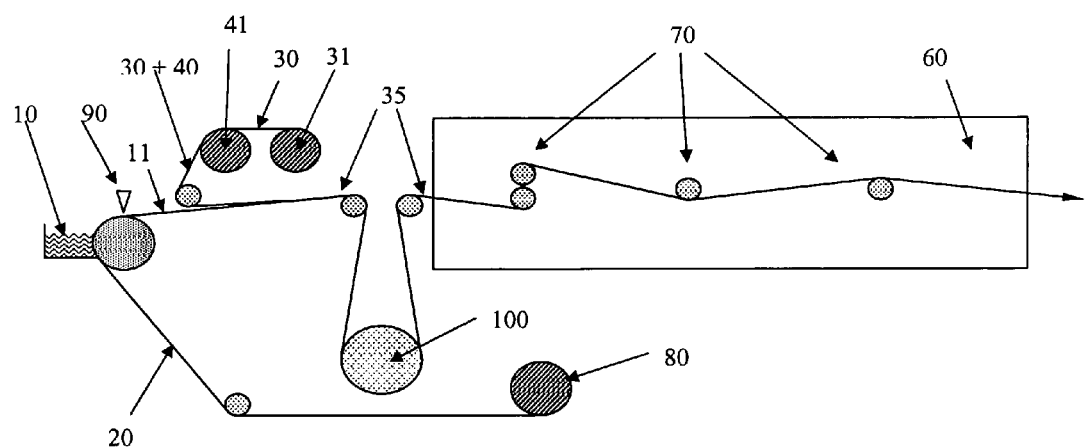
FIG. 6 is a schematic diagram of a preferred embodiment of the present invention (Example 2). The ePTFE membrane 30 is passed over a roll 41 of textile fabric 40 and both membrane 30 and fabric 40 are laid-down onto the PDMS coating 11 simultaneously. Vacuum roll 100 is utilized to apply vacuum to the surface 35 of the textile fabric 40 as it passes over an active vacuum area of approximately 180 degrees (3 o'clock to 9 o'clock position in FIG. 6).
Figure 7:
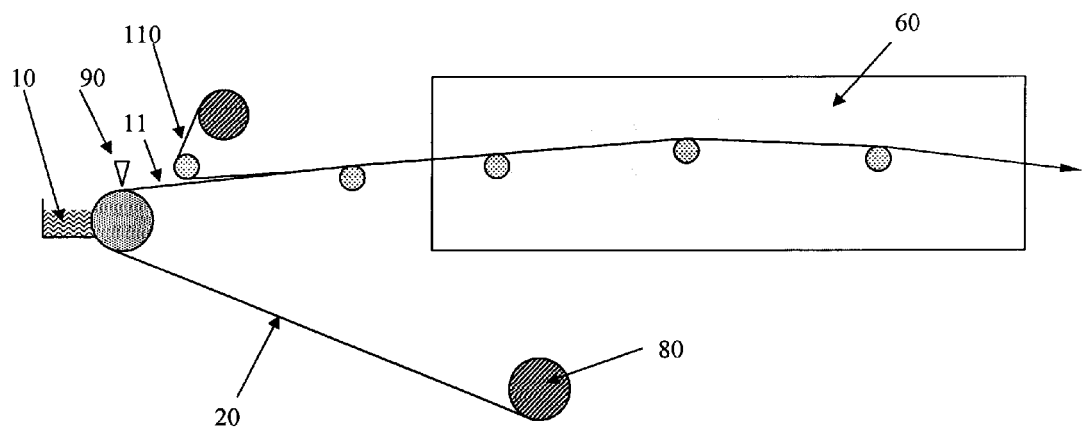
FIG. 7 is a schematic diagram of another preferred embodiment of the present invention (Example 3). With this example the textile fabric is pre-laminated to PTFE film using a hot melt polyurethane adhesive 10b. A roll of the pre-laminated material 110 is unwound onto the liquid silicone and the IPN material is formed in situ.

The process of Example 1 was repeated but the arrangement of the unwind apparatuses was changed (FIG. 6) so that the ePTFE membrane 30 was pulled over the fabric 40 and both materials were brought into contact with the liquid PDMS coating 11 at the same time (FIG. 6). This simplified the unwinding of the ePTFE membrane 30 which is very tension sensitive and subject to mechanical deformation. In addition, a vacuum roller 100 was placed between the lay-down point of the ePTFE/fabric and the entry of the oven 60. The active face of the vacuum roller 100 was deckled to a 12 inch (30 cm) width and a wraparound angle of approximately 180 degrees.

EXAMPLE 3

The process of Example 1 was repeated except that the textile fabric was pre-laminated to ePTFE film off-line using a dot pattern of hot melt polyurethane adhesive 10b. A roll of the pre-laminated material 110 was then unwound onto the liquid silicone with the ePTFE side of the laminate in contact with the silicone. The hot melt adhesive provides a high-quality bond between the PTFE and the textile backing, thereby eliminating the need for a vacuum roller or solvent processing aids. This technique also simplifies the unwind process in that the ePTFE and textile backing are not unwound separately. Although the pre-lamination technique does introduce a preliminary step to the process, reliance on the impregnation efficiency of the silicone on achieving an effective bond with the textile backing is eliminated and no equipment modifications are necessary. The impregnation and bonding process is therefore much less sensitive to line speed and temperature parameters thereby allowing increased production efficiency and offsetting the expense of the pre-lamination step. Any combination of ePTFE pore size and thickness parameters that results in sufficient impregnation of the silicone into the ePTFE to form an IPN structure results in a final product with adequate bond integrity between the IPN material and textile backing.

Figure 2:
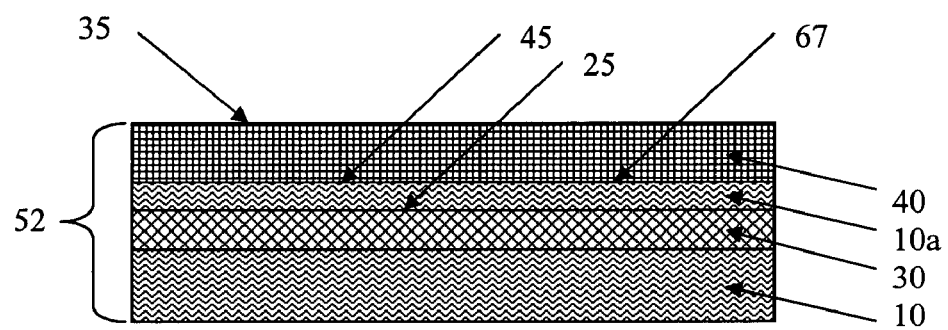
FIG. 2 is a cross-sectional view of a preferred embodiment of the present invention where the PDMS layer 10 is impregnated into an ePTFE membrane 30 and additional PDMS layer 10a is present above the distal or upper surface 25 of the IPN membrane 30 providing high quality bond at interface 45 between layer 10a and fabric 40.
Figure 3:
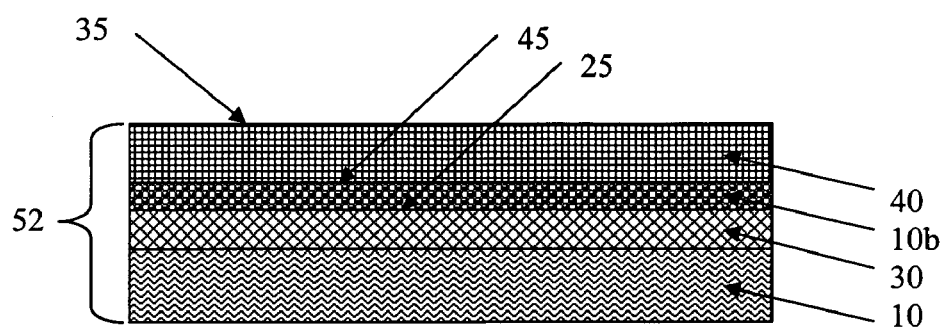
FIG. 3 is a cross-sectional view of a preferred embodiment of the present invention where the PDMS layer 10 is impregnated into an ePTFE membrane 30 which is pre-laminated to a backing fabric 40 using a dot-pattern of adhesive 10b providing high quality bond at interface 45 between layer 10b and fabric 40.
Figure 4:
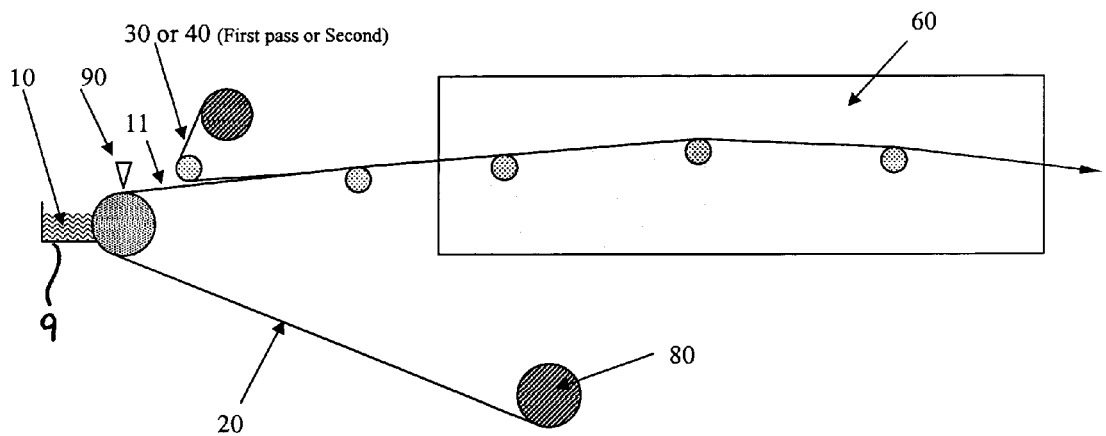
FIG. 4 is a schematic diagram of the prior art process where in a roll 80 of carrier substrate 20 is passed through a reservoir 9 of liquid PDMS 10. Doctor blade 90 meters-off excess PDMS leaving coating 11 and either ePTFE 30 or textile fabric 40 is applied depending on whether it is the first or second pass of the process. The material is then passed through the tunnel oven (60).
Figure 5:
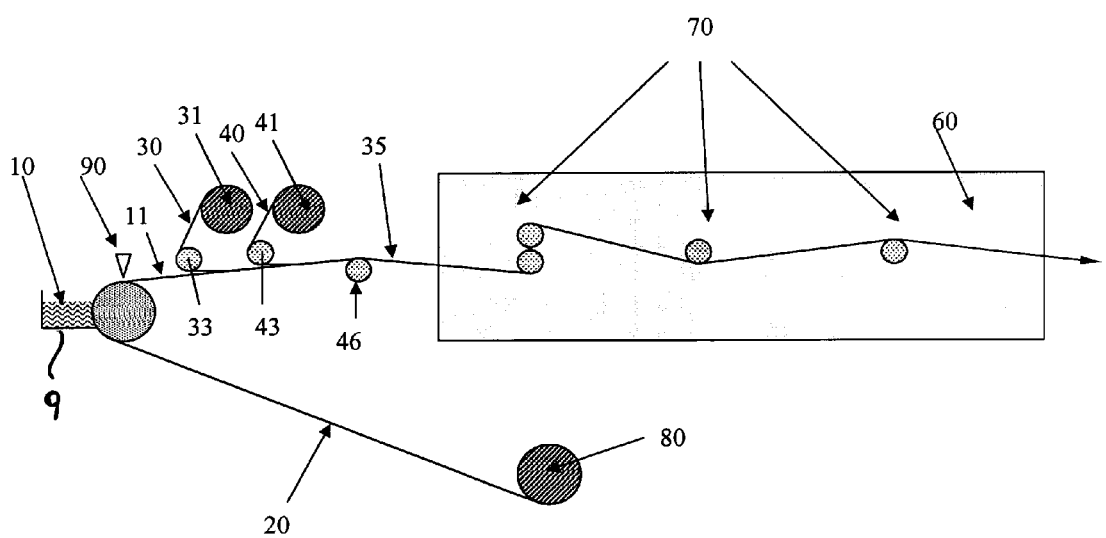
FIG. 5 is a schematic diagram of a preferred embodiment of the present invention (Example 1). The ePTFE sheet 30 is applied to coating 11 on carrier substrate 20 just prior to the textile fabric 40, and the carrier substrate 20 path is serpentined and "S-wrapped" over and under the rollers as shown 70. Upper surface 35 of the textile fabric 40 contacts down-line machine parts such as rollers to avoid sticking.

Each example produced a final fabric composite sheet 52 such as shown in FIG. 2 with a high quality bond between layers and the material could be removed from the backing paper carrier substrate 20 without causing delaminating of the textile fabric layer 40 and the IPN sheet 12.

The invention claimed is:

1. A process of creating an interpenetrating polymer network sheet bonded to a backing material comprising the steps of a) casting a liquid polymer formulation as a coating onto a carrier substrate, b) applying a microporous polymer sheeting membrane to the surface of the coating and allowing or causing said liquid polymer layer to impregnate said microporous polymer membrane, c) applying a backing material to the distal surface of the impregnated membrane, and d) causing a bond to form between the backing material and the impregnated membrane to form a composite sheet, and e) solidifying the liquid polymer formulation,
wherein the composite sheet is formed by curing together in a single pass through an oven, said impregnated membrane and said backing material.

2. The process of claim 1, wherein the liquid polymer formulation is polydimethylsiloxane.

3. The process of claim 1, wherein the microporous polymer membrane is expanded polytetrafluoroethylene.

4. The process of claim 1 wherein the backing material is textile fabric.

5. The process of claim 1, wherein the backing material is foam, a nonwoven film, or material other than a textile fabric.

6. The process of claim 1, wherein the bond between the backing material and the distal or upper surface of the membrane is enhanced by exposure to vacuum by means of a vacuum roller device placed in contact with the distal or upper surface of the backing material prior to solidification of the liquid polymer formulation.

7. The process of claim 1, wherein the liquid polymer formulation layer is polydimethylsiloxane, the microporous polymer membrane is expanded polytetrafluoroethylene, and the backing material is textile fabric.

8. The process of claim 1, wherein the liquid polymer formulation layer is polydimethylsiloxane, the microporous polymer sheet is expanded polytetrafluoroethylene and the backing material is foam, a nonwoven film, or material other than a textile fabric.

9. A process of creating an interpenetrating polymer network sheet bonded to a backing material comprising the steps of a) casting a liquid polymer formulation as a coating onto a carrier substrate, b) applying a lamination of microporous polymer sheeting membrane and backing material to the surface of the coating and allowing or causing said liquid polymer layer to impregnate said microporous polymer membrane, and c) solidifying the liquid polymer formulation;
wherein the composite sheet is formed by curing together in a single pass through an oven, said impregnated membrane and said backing material.

10. The process of claim 9, wherein the liquid polymer formulation is polydimethylsiloxane.

11. The process of claim 9, wherein the microporous polymer membrane is expanded polytetrafluoroethylene.

12. The process of claim 9, wherein the backing material is textile fabric.

13. The process of claim 9, wherein the backing material is foam, a nonwoven film, or material other than a textile fabric.

14. The process of claim 9, wherein the liquid polymer formulation layer is polydimethylsiloxane, the microporous polymer membrane is expanded polytetrafluoroethylene, and the backing layer is textile fabric.

15. The process of claim 9, wherein the liquid polymer formulation layer is polydimethysiloxane, the microporous polymer sheet is expanded polytetrafluoroethylene, and the backing layer is foam, a nonwoven film, or material other than a textile fabric.

16. A method of making a wound dressing or scar management product comprising the steps of
forming a layer of liquid polymer formulation onto a carrier substrate,
laying a layer of microporous polymer sheeting membrane laminated to a backing material on top of the liquid polymer formulation layer,
impregnating the microporous polymer sheeting membrane layer with the liquid polymer formulation by capillary wicking through the small pores in the microporous polymer sheeting forming an interpenetrating polymer network sheet, and
solidifying the liquid polymer formulation by passing in a single pass through an oven, said laminated layer of microporous polymer sheeting membrane, said backing material, and liquid polymer formulation layer.

17. The process of claim 16, wherein the liquid polymer formulation is polydimethylsiloxane.

18. The process of claim 16, wherein the microporous polymer membrane is expanded polytetrafluorethylene.

19. The process of claim 16, wherein the backing material is textile fabric.

20. The process of claim 16, wherein the backing material is foam, a nonwoven film, or material other than a textile fabric.

21. The process of claim 16, wherein the liquid polymer formulation layer is polydimethylsiloxane, the microporous polymer membrane 30 is expanded polytetrafluoroethylene, and the backing layer 40 is textile fabric.

22. The process of claim 16, wherein the liquid polymer formulation layer is polydimethylsiloxane, the microporous polymer sheet 30 is expanded polytetrafluoroethylene, and the backing layer 40 is foam, a nonwoven film, or material other than a textile fabric.

* * * * *